United States Patent [19]
Brown

[11] Patent Number: 5,804,079
[45] Date of Patent: Sep. 8, 1998

[54] SYSTEMS AND METHODS FOR REDUCING THE NUMBER OF LEUKOCYTES IN CELLULAR PRODUCTS LIKE PLATELETS HARVESTED FOR THERAPEUTIC PURPOSES

[75] Inventor: Richard I. Brown, Northbrook, Ill.

[73] Assignee: Baxter International Inc., Deerfield, Ill.

[21] Appl. No.: 719,138

[22] Filed: Sep. 24, 1996

Related U.S. Application Data

[62] Division of Ser. No. 551,579, Nov. 1, 1995, abandoned, which is a continuation of Ser. No. 97,967, Jul. 26, 1993, abandoned, which is a continuation-in-part of Ser. No. 965,088, Oct. 22, 1992, Pat. No. 5,370,802, which is a continuation-in-part of Ser. No. 814,403, Dec. 23, 1991, abandoned.

[51] Int. Cl.$^6$ .......................... B01D 21/26; B01D 36/00; B01D 37/00; A61M 1/38

[52] U.S. Cl. .............................. 210/739; 210/85; 210/86; 210/94; 210/97; 210/109; 210/110; 210/143; 210/252; 210/258; 210/295; 210/435; 210/745; 210/782; 210/787; 210/789; 210/806; 494/1; 494/2; 494/10; 494/36; 494/37; 604/4; 604/5; 604/6; 604/67

[58] Field of Search .................................. 210/739, 744, 210/745, 767, 782, 787, 789, 806, 929, 85, 86, 94, 97, 109, 110, 143, 252, 257.1, 258, 294, 295, 360.1, 418, 435, 446; 604/4, 5, 6, 65, 67; 494/1, 5, 10, 3, 36, 37, 2

[56] References Cited

U.S. PATENT DOCUMENTS

| | | | |
|---|---|---|---|
| Re. 29,738 | 8/1978 | Adams | 359/503 |
| D. 255,935 | 7/1980 | Cullis et al. | D24/58 |
| D. 255,936 | 7/1980 | Cullis et al. | D24/58 |
| D. 258,909 | 4/1981 | Bergo et al. | D24/1.1 |
| D. 314,824 | 2/1991 | Moon | D24/22 |
| 2,848,995 | 8/1958 | Ryan . | |
| 3,064,647 | 11/1962 | Earl . | |
| 3,244,363 | 4/1966 | Hein . | |
| 3,347,454 | 10/1967 | Bellamy, Jr. et al. . | |
| 3,489,145 | 1/1970 | Judson et al. . | |
| 3,519,201 | 7/1970 | Eisel et al. . | |
| 3,561,672 | 2/1971 | Schlutz et al. | 494/1 |
| 3,655,123 | 4/1972 | Judson et al. | 494/10 |
| 3,672,564 | 6/1972 | Schultz et al. | 494/17 |
| 3,701,434 | 10/1972 | Moore | 210/477 |
| 3,737,096 | 6/1973 | Jones et al. | 494/9 |
| 3,748,101 | 7/1973 | Jones et al. . | |
| 3,786,919 | 1/1974 | Deringer | 494/27 |
| 3,802,432 | 4/1974 | Djerassi . | |
| 3,825,175 | 7/1974 | Sartory | 494/27 |
| 3,857,393 | 12/1974 | Rose . | |
| 3,858,796 | 1/1975 | Unger et al. | 494/34 |
| 3,953,329 | 4/1976 | Updike | 210/638 |
| 3,957,197 | 5/1976 | Sartory et al. | 494/1 |

(List continued on next page.)

FOREIGN PATENT DOCUMENTS

| | | |
|---|---|---|
| 1303702 | 6/1992 | Canada . |
| 1304309 | 6/1992 | Canada . |
| WO 91/15300 | 10/1991 | WIPO . |

OTHER PUBLICATIONS

"The Physics of Continuous Flow Centrifugal Cell Separation", Artifical Organs, Richard I. Brown, 13(1):4–20, Raven Press 1989.

*Primary Examiner*—John Kim
*Attorney, Agent, or Firm*—Daniel D. Ryan; Denise M. Serewicz; Bradford R. L. Price

[57] ABSTRACT

Systems and methods separate whole blood containing leukocytes in a first separation chamber into a first layer comprising red blood cells, a second layer comprising a suspension of platelets, and an interface between the first and second layers. The systems and methods convey the suspension of platelets into a second separation chamber while simultaneously filtering the suspension of platelets to reduce the number of leukocytes. The systems and methods separate the filtered suspension of platelets in the second separation chamber into a platelet-rich concentrate and platelet-poor component.

6 Claims, 7 Drawing Sheets

U.S. PATENT DOCUMENTS

| | | | |
|---|---|---|---|
| 3,964,467 | 6/1976 | Rose . | |
| 3,986,506 | 10/1976 | Garber et al. . | |
| 3,987,961 | 10/1976 | Sinn et al. | 494/45 |
| 4,007,871 | 2/1977 | Jones et al. | 494/45 |
| 4,010,894 | 3/1977 | Kellogg et al. | 494/45 |
| 4,013,564 | 3/1977 | Nose | 210/434 |
| 4,025,618 | 5/1977 | Garber et al. . | |
| 4,056,224 | 11/1977 | Lolachi | 494/18 |
| 4,091,989 | 5/1978 | Schlutz | 494/27 |
| 4,094,461 | 6/1978 | Kellogg et al. | 494/81 |
| 4,098,456 | 7/1978 | Bayham | 494/17 |
| 4,108,353 | 8/1978 | Brown | 494/18 |
| 4,109,852 | 8/1978 | Brown et al. | 494/18 |
| 4,109,854 | 8/1978 | Brown | 494/18 |
| 4,109,855 | 8/1978 | Brown et al. | 494/18 |
| 4,111,356 | 9/1978 | Boggs et al. | 494/18 |
| 4,113,173 | 9/1978 | Lolachi | 494/18 |
| 4,114,802 | 9/1978 | Brown | 494/18 |
| 4,120,448 | 10/1978 | Callis | 494/43 |
| 4,120,449 | 10/1978 | Brown et al. | 494/18 |
| 4,127,231 | 11/1978 | Khoja et al. | 494/1 |
| 4,142,670 | 3/1979 | Ishimaru et al. | 494/38 |
| 4,146,172 | 3/1979 | Cullis et al. | 604/410 |
| 4,164,318 | 8/1979 | Boggs | 494/18 |
| 4,185,629 | 1/1980 | Cullis et al. | 604/6 |
| 4,187,979 | 2/1980 | Cullis et al. | 494/1 |
| 4,191,182 | 3/1980 | Popovich et al. | 210/90 |
| 4,194,684 | 3/1980 | Boggs | 494/18 |
| 4,215,688 | 8/1980 | Terman et al. | 604/5 |
| 4,216,770 | 8/1980 | Cullis et al. | 604/6 |
| 4,223,672 | 9/1980 | Terman et al. | 210/782 |
| 4,230,263 | 10/1980 | Westberg | 494/45 |
| 4,235,233 | 11/1980 | Mouwen . | |
| 4,244,513 | 1/1981 | Fayer et al. | 494/10 |
| 4,246,107 | 1/1981 | Takenaka et al. | 210/806 |
| 4,261,507 | 4/1981 | Baumler | 494/45 |
| 4,266,717 | 5/1981 | Jennings et al. . | |
| 4,269,718 | 5/1981 | Persidsky | 210/787 |
| 4,278,201 | 7/1981 | Cailliot | 494/84 |
| 4,278,202 | 7/1981 | Westberg | 494/45 |
| 4,278,592 | 7/1981 | Seufert | 210/782 |
| 4,283,004 | 8/1981 | Lamadrid | 494/60 |
| 4,283,276 | 8/1981 | Grant | 494/10 |
| 4,316,576 | 2/1982 | Cullis et al. | 494/21 |
| 4,321,192 | 3/1982 | Jain | 210/647 |
| 4,322,275 | 3/1982 | Jain . | |
| 4,330,080 | 5/1982 | Mathieu | 494/43 |
| 4,330,410 | 5/1982 | Takenaka et al. | 210/767 |
| 4,343,705 | 8/1982 | Legg | 210/637 |
| 4,344,560 | 8/1982 | Iriguchi et al. | 210/96.1 |
| 4,350,156 | 9/1982 | Malchesky et al. | 210/434 |
| 4,350,283 | 9/1982 | Leonian | 422/72 |
| 4,353,795 | 10/1982 | Romanauskas | 209/155 |
| 4,357,235 | 11/1982 | Dilks, Jr. | 209/155 |
| 4,379,452 | 4/1983 | DeVries | 604/6 |
| 4,386,730 | 6/1983 | Mulzet | 494/81 |
| 4,387,848 | 6/1983 | Kellogg et al. | 494/81 |
| 4,402,680 | 9/1983 | Schoendorfer | 494/3 |
| 4,405,079 | 9/1983 | Schoendorfer | 494/1 |
| 4,411,792 | 10/1983 | Babb | 210/651 |
| 4,416,777 | 11/1983 | Kuroda et al. | 210/446 |
| 4,419,089 | 12/1983 | Kolobow et al. | 494/45 |
| 4,421,503 | 12/1983 | Latham, Jr. et al. | 494/17 |
| 4,425,112 | 1/1984 | Ito | 494/18 |
| 4,430,072 | 2/1984 | Kellogg et al. | 494/45 |
| 4,432,871 | 2/1984 | Yamawaki et al. | 210/195.1 |
| 4,445,883 | 5/1984 | Schoendorfer | 494/21 |
| 4,446,014 | 5/1984 | Dilks, Jr. et al. | 494/27 |
| 4,446,015 | 5/1984 | Kirkland | 494/27 |
| 4,447,221 | 5/1984 | Mulzet | 494/45 |
| 4,448,679 | 5/1984 | Dilks, Jr. et al. | 494/27 |
| 4,464,167 | 8/1984 | Schoendorfer et al. | 604/6 |
| 4,482,342 | 11/1984 | Lueptow et al. | 494/21 |
| 4,493,691 | 1/1985 | Calari | 494/10 |
| 4,512,763 | 4/1985 | Schneider | 604/5 |
| 4,530,691 | 7/1985 | Brown | 494/45 |
| 4,531,932 | 7/1985 | Luppi et al. | 604/6 |
| 4,605,503 | 8/1986 | Bilstad et al. | 210/651 |
| 4,609,461 | 9/1986 | Takata et al. | 210/195.2 |
| 4,627,915 | 12/1986 | Kuroda et al. | 210/195.2 |
| 4,636,193 | 1/1987 | Cullis | 494/45 |
| 4,647,279 | 3/1987 | Mulzet et al. | 494/45 |
| 4,648,866 | 3/1987 | Malbrancq et al. | 604/5 |
| 4,655,742 | 4/1987 | Vantard | 604/6 |
| 4,670,002 | 6/1987 | Koreeda et al. | 494/10 |
| 4,675,117 | 6/1987 | Neumann et al. | 210/789 |
| 4,680,025 | 7/1987 | Kruger et al. | 604/6 |
| 4,708,712 | 11/1987 | Mulzet | 494/45 |
| 4,710,161 | 12/1987 | Takabayashi et al. | 494/84 |
| 4,724,317 | 2/1988 | Brown et al. | 494/10 |
| 4,729,829 | 3/1988 | Duggins | 210/195.2 |
| 4,734,089 | 3/1988 | Cullis | 494/27 |
| 4,743,227 | 5/1988 | Takeuchi | 494/85 |
| 4,747,952 | 5/1988 | Nakano et al. | 210/782 |
| 4,767,541 | 8/1988 | Wisdom | 210/749 |
| 4,769,150 | 9/1988 | Ramstack | 210/636 |
| 4,776,964 | 10/1988 | Schoendorfer et al. | 210/782 |
| 4,789,482 | 12/1988 | DiLeo et al. | 240/651 |
| 4,790,807 | 12/1988 | Neumann et al. | 494/45 |
| 4,806,252 | 2/1989 | Brown et al. | 210/744 |
| 4,810,378 | 3/1989 | Carmen et al. | 210/446 |
| 4,834,890 | 5/1989 | Brown et al. | 210/739 |
| 4,850,995 | 7/1989 | Tie et al. | 604/6 |
| 4,851,126 | 7/1989 | Schoendorfer | 210/651 |
| 4,855,057 | 8/1989 | Ohnishi et al. | 210/650 |
| 4,857,190 | 8/1989 | Wada et al. | 210/232 |
| 4,871,462 | 10/1989 | Fischel et al. | 210/651 |
| 4,897,185 | 1/1990 | Schuyler et al. | 210/90 |
| 4,900,298 | 2/1990 | Langley | 494/82 |
| 4,911,833 | 3/1990 | Schoendorfer et al. | 210/782 |
| 4,915,683 | 4/1990 | Sieber | 604/4 |
| 4,915,848 | 4/1990 | Carmen et al. | 210/749 |
| 4,919,823 | 4/1990 | Wisdom | 210/749 |
| 4,923,439 | 5/1990 | Seidel et al. | 604/6 |
| 4,934,995 | 6/1990 | Cullis | 494/45 |
| 4,936,820 | 6/1990 | Dennehey et al. | 494/1 |
| 4,943,287 | 7/1990 | Carmen | 210/206 |
| 4,968,295 | 11/1990 | Neumann | 604/6 |
| 4,975,186 | 12/1990 | Wada et al. | 210/232 |
| 4,985,153 | 1/1991 | Kuroda et al. | 210/782 |
| 4,990,132 | 2/1991 | Unger et al. | 604/6 |
| 5,006,103 | 4/1991 | Bacehowski et al. | 494/45 |
| 5,045,185 | 9/1991 | Ohnaka et al. | 210/86 |
| 5,067,938 | 11/1991 | Uchida et al. | 494/12 |
| 5,076,911 | 12/1991 | Brown et al. | 210/94 |
| 5,089,146 | 2/1992 | Carmen et al. | 210/782 |
| 5,089,417 | 2/1992 | Wogoman | 436/45 |
| 5,092,996 | 3/1992 | Spielberg | 210/232 |
| 5,100,564 | 3/1992 | Pall et al. | 210/782 |
| 5,104,526 | 4/1992 | Brown et al. | 210/94 |
| 5,104,788 | 4/1992 | Carmen et al. | 435/2 |
| 5,135,667 | 8/1992 | Schoendorfer | 210/782 |
| 5,154,716 | 10/1992 | Bauman et al. | 604/4 |
| 5,171,456 | 12/1992 | Hwang et al. | 210/782 |
| 5,194,145 | 3/1993 | Schoendorfer | 210/90 |
| 5,217,426 | 6/1993 | Bachekowski et al. | 494/45 |
| 5,217,427 | 6/1993 | Cullis | 494/45 |
| 5,217,627 | 6/1993 | Pall et al. | 210/767 |
| 5,229,012 | 7/1993 | Pall et al. | 210/767 |
| 5,234,608 | 8/1993 | Duff | 210/806 |
| 5,236,716 | 8/1993 | Carmen et al. | 210/782 |
| 5,288,403 | 2/1994 | Ohno | 210/508 |

| | | | |
|---|---|---|---|
| 5,300,019 | 4/1994 | Bischof et al. | 604/4 |
| 5,370,802 | 12/1994 | Brown | 210/782 |
| 5,399,268 | 3/1995 | Pall et al. | 210/767 |
| 5,427,695 | 6/1995 | Brown | 210/805 |
| 5,437,624 | 8/1995 | Langley | 604/4 |
| 5,501,795 | 3/1996 | Pall et al. | 210/508 |
| 5,512,187 | 4/1996 | Buchholz et al. | 210/767 |
| 5,529,691 | 6/1996 | Brown | 210/94 |
| 5,536,238 | 7/1996 | Bischof | 604/6 |
| 5,545,516 | 8/1996 | Wagner | 435/2 |
| 5,547,591 | 8/1996 | Hagihara et al. | 210/782 |
| 5,549,834 | 8/1996 | Brown | 210/806 |
| 5,591,337 | 1/1997 | Lynn et al. | 210/489 |

SYSTEMS AND METHODS FOR REDUCING THE NUMBER OF LEUKOCYTES IN CELLULAR PRODUCTS LIKE PLATELETS HARVESTED FOR THERAPEUTIC PURPOSES

This is a divisional of application Ser. No. 08/551,579 filed Nov. 1, 1995, abandoned, which is a continuation of application Ser. No. 08/097,967 filed on Jul. 26, 1993 abandoned; which is a continuation-in-part of application Ser. No. 07/965,088 filed Oct. 22, 1992, now U.S. Pat. No. 5,370,802; which is itself a continuation-in-part of application Ser. No. 07/814,403 filed Dec. 23, 1991, abandoned.

FIELD OF THE INVENTION

The invention generally relates to blood processing systems and methods. In a more specific sense, the invention relates to systems and methods for removing leukocytes from blood components collected for therapeutic purposes.

BACKGROUND OF THE INVENTION

Today blood collection organizations routinely separate whole blood into its various therapeutic components, such as red blood cells, platelets, and plasma.

One separation technique that is in widespread use today uses a multiple blood bag system. The bag system includes a primary blood bag and one or more transfer bags, which are integrally connected to the primary bag by tubing. The technique collects from a donor a single unit (about 450 ml) of whole blood in the primary blood bag. The donor is then free to leave.

The donor's whole blood later undergoes centrifugal separation within the primary bag into red blood cells and plasma rich in platelets. The plasma rich in platelets is expressed out of the primary bag into a transfer bag, leaving the red blood cells behind. The plasma rich in platelets then undergoes further centrifugal separation within the transfer bag into a concentration of platelets and plasma poor in platelets. The plasma poor in platelets is expressed from the transfer bag into another transfer bag, leaving the concentration of platelets behind.

Using multiple blood bag systems, all three major components of whole blood can be collected for therapeutic use. However, the yield for each component collected is limited to the volume of the components that are contained in a single unit of whole blood. Furthermore, because red blood cells are retained, United States governmental regulations prohibit collecting another unit of whole blood from the donor until six weeks later.

Certain therapies transfuse large volumes of a single blood component. For example, some patients undergoing chemotherapy require the transfusion of large numbers of platelets on a routine basis. Multiple blood bag systems simply are not an efficient way to collect these large numbers of platelets from individual donors.

On line blood separation systems are today used to collect large numbers of platelets to meet this demand. On line systems perform the separation steps necessary to separate a concentration of platelets from whole blood in a sequential process with the donor present. On line systems establish a flow of whole blood from the donor, separate out the desired platelets from the flow, and return the remaining red blood cells and plasma to the donor, all in a sequential flow loop.

Large volumes of whole blood (for example, 2.0 liters) can be processed using an on line system. Due to the large processing volumes, large yields of concentrated platelets (for example, $4 \times 10^{11}$ platelets suspended in 200 ml of fluid) can be collected. Moreover, since the donor's red blood cells are returned, the donor can donate whole blood for on line processing much more frequently than donors for processing in multiple blood bag systems.

Nevertheless, a need still exists for further improved systems and methods for collecting cellular-rich concentrates from blood components in a way that lends itself to use in high volume, on line blood collection environments, where higher yields of critically needed cellular blood components like platelets can be realized.

SUMMARY OF THE INVENTION

One aspect of the invention provides systems and methods that employ three in-line separation devices for obtaining a platelet-rich concentrate having a reduced number of leukocytes. The systems and methods introduce whole blood containing leukocytes from a source at a selected first pumping rate into a first separation chamber. The systems and methods separate the whole blood in the first separation chamber into a first layer comprising red blood cells, a second layer comprising a suspension of platelets, and an interface between the first and second layers. The systems and methods convey the suspension of platelets at an outlet pumping rate from the first separation chamber into a second separation chamber while simultaneously filtering the suspension of platelets to reduce the number of leukocytes. The systems and methods monitor the location of the interface within the first separation chamber and vary the outlet pumping rate to maintain the interface within the first separation chamber while conveying the suspension of platelets from the first separation chamber. The systems and methods separate the filtered suspension of platelets in the second separation chamber into a platelet-rich concentrate and platelet-poor component.

DESCRIPTION OF THE PREFERRED EMBODIMENTS

Figure 1:
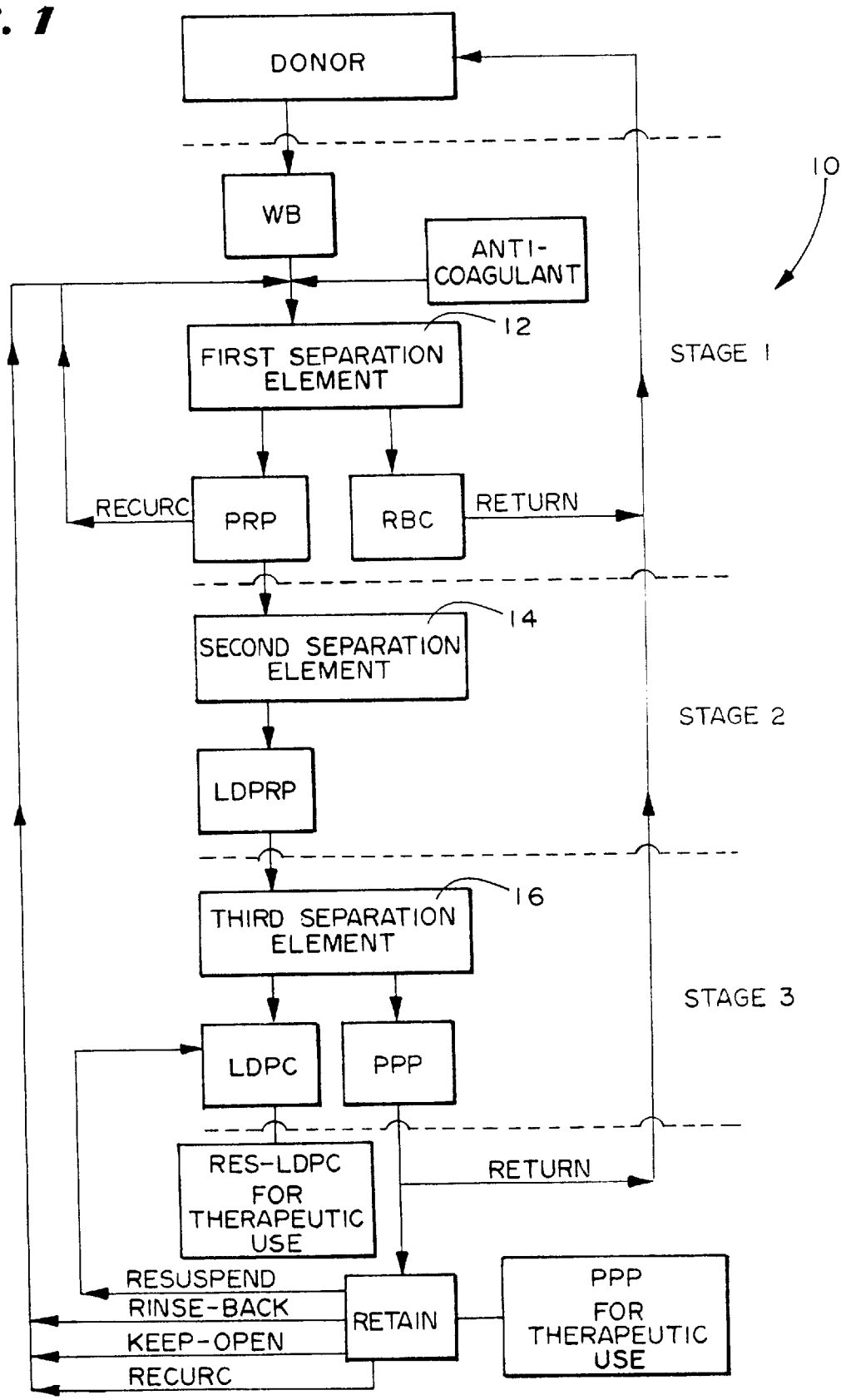
FIG. 1 is a diagrammatic view of a three stage blood processing system that embodies the features of the invention.

FIG. 1 shows in diagrammatic form a multiple stage blood processing system 10 that embodies the features of the invention.

In use, the system 10 draws whole blood (WB) from a donor, while adding anticoagulant. The system 10 ultimately separates the anticoagulated WB into three end products.

The first end product is red blood cells (RBC). The second end product is a platelet-poor component, which is commonly called platelet-poor plasma (PPP). The third end product is a resuspended, leukocyte-depleted platelet concentrate (RES-LDPC).

The system 10 returns RBC to the donor. The system 10 retains RES-LDPC for long term storage and subsequent therapeutic use. The system 10 returns a portion of the PPP to the donor. According to one aspect of the invention, the system 10 retains the rest of the PPP for various processing purposes and for long term storage for therapeutic purposes.

The system 10 employs three separation stages to create these three end products.

In the first separation stage, the system 10 directs anticoagulated WB from the donor into a first separation element 12. The first element 12 separates the whole blood into RBC and an intermediate product, which constitutes a platelet suspension.

This platelet suspension is typically plasma rich in platelets, and it is commonly referred to as platelet-rich plasma (PRP). However, as used in this Specification, the term "platelet suspension" is not limited to PRP in the technical sense. The term "platelet suspension" is intended to encompass any suspension in which platelets are present in concentrations greater than in whole blood, and can include suspensions that carry other blood components in addition to platelets.

In the second separation stage, the system 10 directs PRP into a second separation element 14. The second element 14 reduces the number of leukocytes from the PRP, creating another intermediate product, which constitutes leukocyte depleted PRP (LDPRP).

As used in this Specification, the term "leukocyte depleted" does not denote that all or substantially all the leukocytes have been removed. The term is intended to more broadly indicate only that the number of leukocytes have been reduced by some active separation process.

In the illustrated and preferred embodiment, the system 10 diverts a portion of PRP exiting the first element 12 away from the second separation element 14. This diverted flow of PRP is recirculated back into the first separation element 12. The recirculated PRP joins the WB entering the first separation element 12.

In the third separation stage, the system 10 directs LDPRP into a third separation element 16. The third element 16 separates LDPRP into another intermediate product, which consists of leukocyte depleted platelet concentrate (LDPC) and PPP.

As used in this Specification, the term "platelet concentrate" is not limited to PC in the technical sense. The term "platelet concentrate" is intended to encompass a volume of platelets that results after a "platelet suspension" (as that term is used in this Specification) undergoes a subsequent separation step that reduces the fluid volume of the platelet suspension.

In the illustrated and preferred embodiment, the system 10 returns some of the PPP to the donor during the processing period. The system 10 retains the rest of the PPP during the processing period.

The system 10 uses the retained PPP in various transitional processing modes.

In one transitional mode, the system 10 adds retained PPP to LDPC. The PPP resuspends the LDPC, creating the RES-LDPC end product. The PPP serves as storage medium for the RES-LDPC during long term storage. However, RES-LDPC can be used for therapeutic use without long term storage.

In another transitional mode, the system 10 uses the retained PPP as an anticoagulated fluid to rinse resident RBC from the system 10 after processing for return to the donor.

In still another transitional mode, the system 10 uses the retained PPP as an anticoagulated fluid to keep fluid lines open and patent during temporary interruptions in processing activity.

In still another transitional mode, the system 10 recirculates the retained PPP to mix with WB entering the first separation element 12. The mixing of retained PPP with WB improves the separation of RBC and PRP in the first element 12.

The system 10 collects the remaining retained PPP for therapeutic purposes, with or without long term storage.

EXAMPLE 1

The exact constitution of the various blood products created by the system 10 during process varies according to the particular physiology of the whole blood donor. Furthermore, as above indicated, the terminology used in this Specification is not intended to be restrictive.

Still, this Example is provided to describe for purposes of illustration the constitution of the blood products that can be obtained from a healthy donor.

A typical healthy donor has a WB hematocrit (Hct) of between 40% (0.4) and 50% (0.5) before donating WB. The hematocrit indicates the volume of RBC per unit volume of WB.

The healthy donor's WB also contains about 250,000 platelets for each microliter ($\mu$l) of plasma.

After separation in the first separation device 12, a portion of the plasma accompanies the RBC that is returned to the donor. As a result, the remaining platelet suspension (PRP) contains a higher concentration of platelets than WB.

In PRP obtained from the typical donor, there are about 350,000 to 400,000 platelets for each $\mu$l of plasma.

The number of platelets per ml of PRP can also be accurately estimated using the following general expression:

$$\text{Platelets}_{PRP} = \text{Platelets}_{WB}\left[\frac{1}{1-Hct}\right]$$

where $\text{Platelets}_{PRP}$ is the concentration (in number per $\mu$l) of platelets in the donor's PRP;

where $\text{Platelets}_{WB}$ is the concentration (in number per $\mu$l) of platelets in the donor's WB before donation; and where Hct is the predonation hematocrit of the donor's WB.

Essentially all the platelets carried in PRP entering the third separate element 16 are there separated from the plasma. The resulting LDPC takes the consistency of a thick fluid-poor "paste" that carries an extremely high concentration of platelets (approximately 30,000,000 to 40,000,000 platelets per $\mu$l).

The LDPC is preferably resuspensed in about 200 $\mu$l of PPP to form RES-LDPC. The resulting RES-LDPC contains about 2,000,000 platelets per ml resuspended in this fluid volume.

In the illustrated and preferred embodiment, the system 10 comprises, once sterilized, a sterile, "closed" system, as judged by the applicable standards in the United States. Furthermore, the system 10 remains "closed" during processing. This assures that the longest authorized storage intervals can be used for the components collected.

As will soon be apparent, the system 10 also lends itself to on line and/or continuous blood separation processes.

The system 10 having the benefits of the invention can be variously constructed.

In the illustrated and preferred embodiments, the system 10 separates blood components in both the first and third elements 12 and 16 using centrifugation techniques. Still, it should be appreciated that other separation techniques could be used for these purposes.

For example, the system 10 can employ centrifugal separation techniques in conjunction with the first element 12 and employ membrane separation techniques in conjunction with the third element 16. Such two stage processing techniques using a combination of centrifugal and membrane separation are disclosed in Schoendorfer U.S. Pat. No. 4,851,126 and Kruger et al. U.S. Pat. No. 4,680,025.

Figure 2:
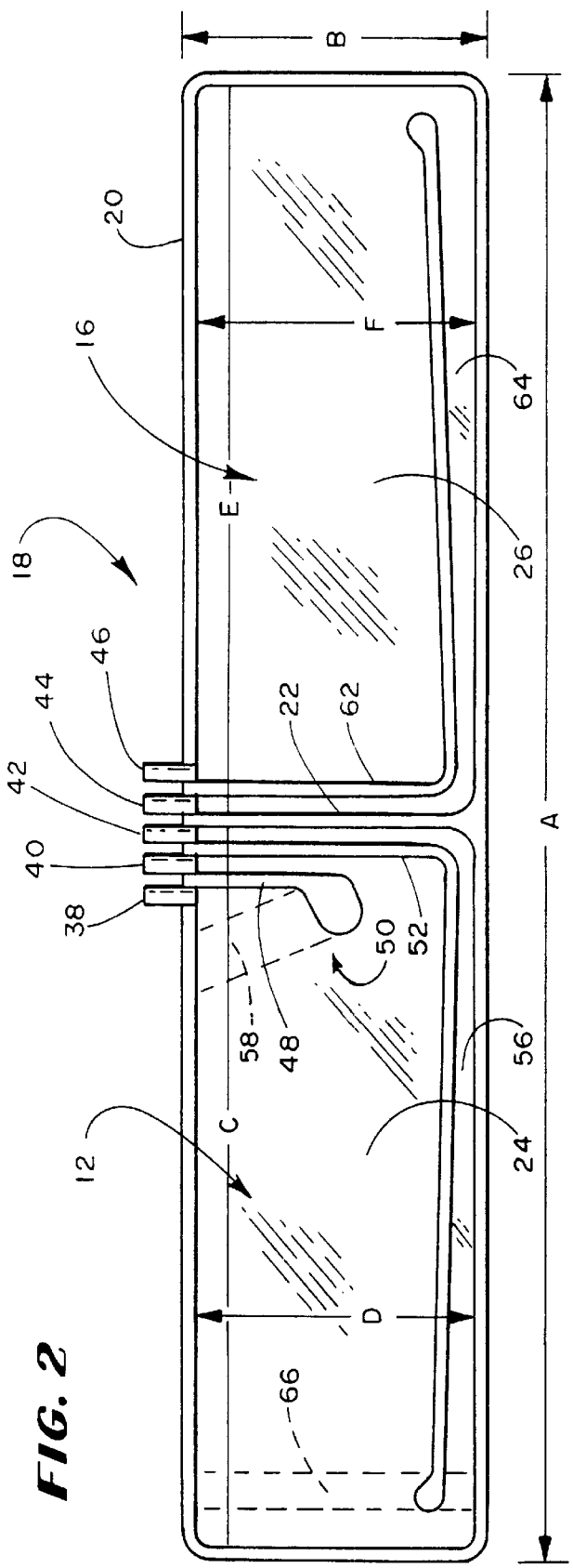
FIG. 2 is a plan side view of a blood processing assembly that integrates two separation elements of the system shown in FIG. 1.
Figure 3:
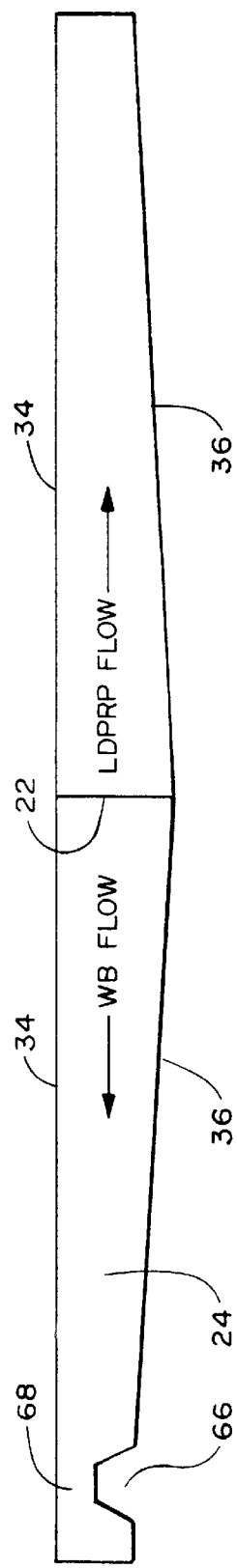
FIG. 3 is a top view of the two element assembly shown in FIG. 2.
Figure 4:
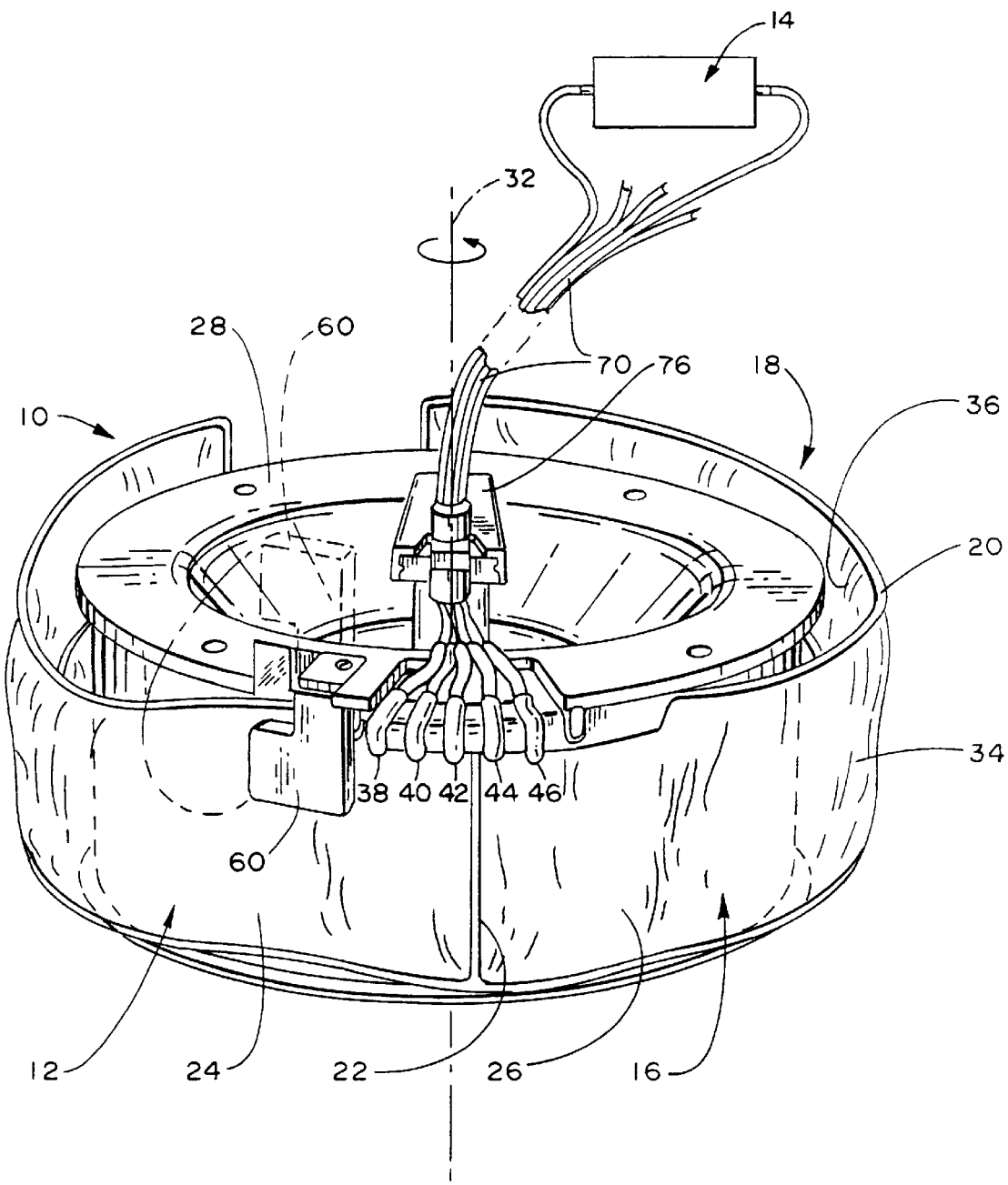
FIG. 4 is a perspective view of the two element assembly shown in FIG. 2, being partially wrapped upon a centrifuge rotor for use and in association with the remaining separation element of the system.

In the particular preferred embodiment shown in FIGS. 2 to 4, the system 10 integrates the first and third elements 12 and 16 into a single centrifugal processing chamber assembly 18. Alternatively, the first and third elements 12 and 16 could comprise physically separate processing chambers.

In the illustrated and preferred embodiment (best seen in FIG. 4), a chamber assembly 18 is formed of two sheets of flexible medical grade plastic joined along their outer edge by a first peripheral seal 20 (see FIG. 2, also).

A second interior seal 22 divides the assembly 18 into a first processing compartment 24 and a second processing compartment 26. Although part of an integral assembly 18, each processing compartment 24 and 26 actually serves as a separate and distinct separation element.

More particularly, the first compartment 24 comprises the first processing element 12. Here, centrifugal forces separate whole blood into RBC and PRP.

The second compartment 26 comprises the third processing element 16. Here, centrifugal forces separate LDPRP into LDPC and PPP.

Further details of the chamber assembly 18 are set forth in copending U.S. patent application Ser. No. 07/965,088, filed Oct. 22, 1992 and entitled "Enhanced Yield Platelet Collection Systems and Methods." This application is incorporated into this Specification by reference.

Figure 5:
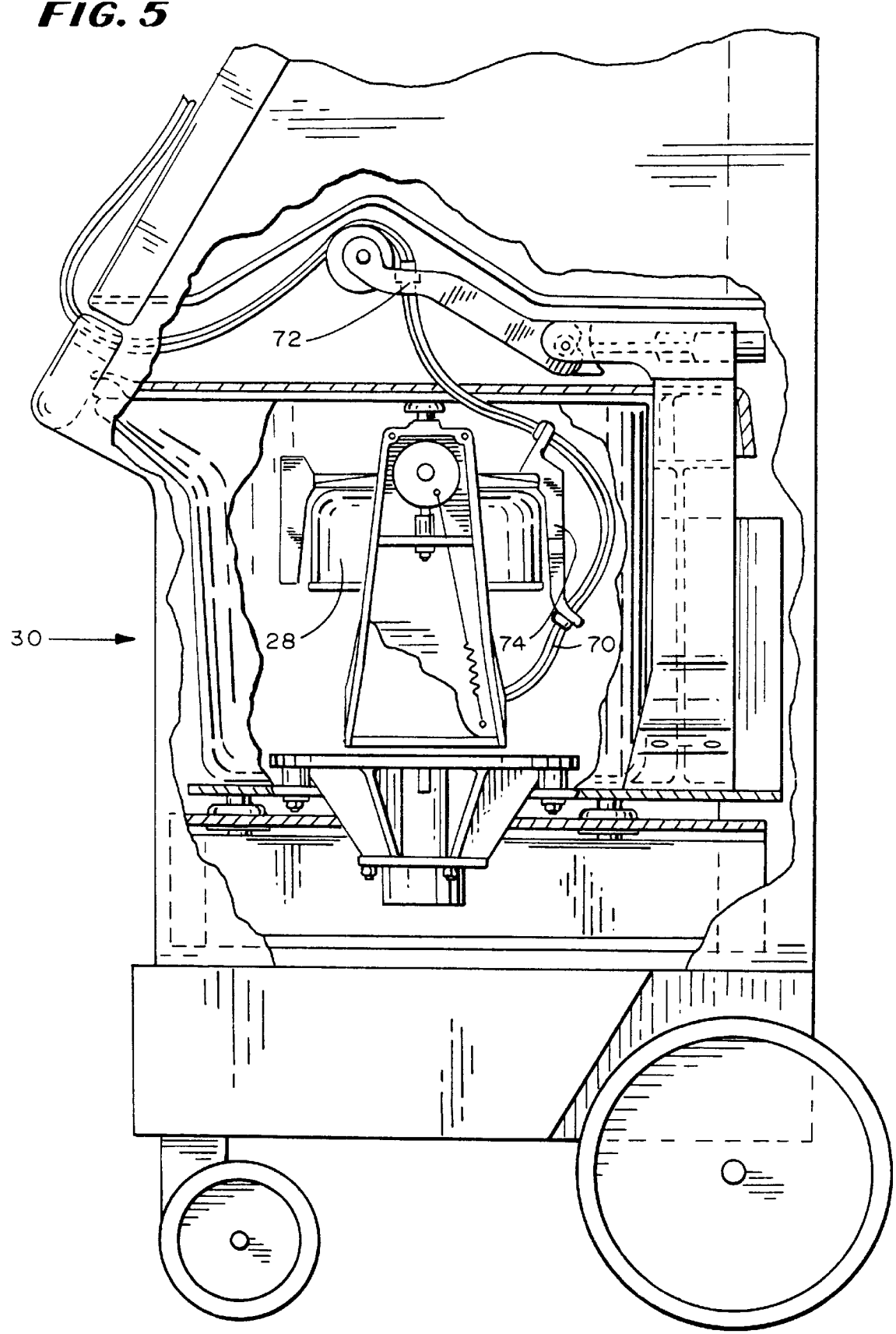
FIG. 5 is a side view, with portions broken away and in section, of a centrifuge for rotating the assembly shown in FIG. 4.

In use, the chamber assembly 18 is wrapped about a rotor 28 of a centrifuge 30 (see FIGS. 4 and 5).

The rotor 28 rotates about an axis 32 to generate centrifugal forces. The centrifugal field extends radially from the axis 32 through each compartment 24 and 26. The compartment wall radially spaced farther from the axis 32 will be called the high-G wall 34 (see FIGS. 3 and 4). The compartment wall radially spaced closer to the axis 32 will be called the low-G wall 36.

The assembly 18 establishes a circumferential flow of fluid during processing. That is, the fluid introduced into each compartment 24 and 26 during rotation follows a circumferential flow path in the compartment 24 and 26 about the rotational axis 32.

In response to the centrifugal forces generated in the first compartment 24, the higher density RBC move toward the high-G wall 34, displacing the lighter density PRP toward the low-G wall 36 of the first compartment 24. An intermediate layer called the interface forms between the RBC and PRP. The interface constitutes the transition between the formed cellular blood components and the liquid plasma component.

Large amounts of leukocytes populate the interface. When dynamic forces within the compartment 24 are not optimized, platelets, too, can settle out of the PRP and onto the interface.

In response to the centrifugal forces generated in the second compartment 26, the higher density platelets in the PRP move toward the high-G wall 34. They displace the lighter density liquid PPP toward the low-G wall 36 of the second compartment 26.

The construction and operation of the centrifuge 30 can vary. Further details of the centrifuge 30 are set forth in copending U.S. patent application Ser. No. 07/814,403, filed Dec. 23, 1991 and entitled "Centrifuge with Separable Bowl and Spool Elements Providing Access to the Separation Chamber". This application is incorporated into this Specification by reference.

Five ports 38/40/42/44/46 open into the compartmentalized areas of the processing assembly 18. The ports 38/40/42/44/46 are arranged side-by-side along the top transverse edge of the respective chamber 24 and 26. Three ports 38/40/42 serve the first chamber 24. Two ports 44/46 serve the second chamber 26.

The first port 38 comprises a PRP collection port. The second port 40 comprises a WB inlet port. The third port 42 comprises a RBC collection port. The fourth port 44 constitutes a PPP collection port. The fifth port 46 constitutes a LDPRP inlet port.

The first chamber 24 includes a third interior seal 48 (see FIG. 2) located between the PRP collection port 38 and the WB inlet port 40. The third seal 48 extends generally parallel to the second interior seal 22 and then bends in a dog-leg away from the WB inlet port 40. The dog-leg terminates beneath the inlet of the PRP collection port 38. The third interior seal 48 forms a PRP collection region 50 within the first chamber 24.

The first chamber 24 also includes a fourth interior seal 52 located between the WB inlet port 40 and the RBC collection port 42. The fourth seal 52 extends generally parallel to the second and third interior seals 22 and 48 and then bends in a dog-leg away from the RBC collection port 42. The dog leg terminates near the longitudinal side edge of the first chamber 24 opposite to the longitudinal side edge formed by the second interior seal 22.

Together, the third and forth interior seals 48/52 form a WB inlet passage 54. Together, the fourth interior seal 52, the second interior seal 22, and the lower regions of the first peripheral seal 20 form a RBC collection passage 56.

The WB inlet passage 54 channels WB directly from the WB inlet port 40 into the flow path at one end of the first chamber 24. WB enters the circumferential flow path immediately next to the PRP collection region 50. Here, the radial flow rates of plasma are greatest, to lift platelets free of the interface and into the PRP collection region 50.

The RBC collection passage 56 receives RBC at the opposite end of the intended circumferential flow path for WB within the chamber 24. From there, the RBC collection passage 56 channels the RBC back to the RBC collection port 42.

A ramp 58 (see FIG. 2) extends from the high-G wall 34 of the first compartment 24 across the PRP collection region 50. The ramp 58 forms a tapered wedge that restricts the flow of fluid toward the PRP collection port 38.

The ramp 58 also orients the interface between RBC and PRP formed during separation for viewing through a side wall of the chamber assembly 18 by an associated interface controller (not shown). The interface controller monitors the location of the interface on the ramp 58 and varies the rate at which PRP is drawn from the chamber 24. This holds the interface at a prescribed location on the ramp 58, keeping RBC, white blood cells, and lymphocytes away from the PRP collection port 38.

In the illustrated embodiment, a hinged flap 60 (see FIG. 4) extends from and overhangs a portion of the rotor. The flap 60 is preformed to present the desired contour of the ramp 58.

Further details of interface control using the ramp 130 are shown in Brown U.S. Pat. No. 4,834,890, as well as in copending U.S. patent application Ser. No. 07/965,088, filed Oct. 22, 1992 and entitled "Enhanced Yield Platelet Collection Systems and Methods." Both are incorporated into this Specification by reference.

The second compartment 26 includes a fifth interior seal 62 (see FIG. 2) that extends between the LDPRP inlet port 46 and the PPP collection port 44. The fifth seal 62 extends generally parallel to the second seal 22 and then bends in a dog-leg away from the LDPRP inlet port 46 in the direction of circumferential PRP flow within the second chamber 26. The dog-leg terminates near the longitudinal side edge of the second chamber 26 opposite to the longitudinal side edge formed by the second interior seal 22.

The fifth interior seal 62, the second interior seal 22, and the lower regions of the first peripheral seal 20 together form a PPP collection passage 64. The PPP collection passage 64 receives PPP at its open end and, from there, channels the PPP to the PPP collection port 44.

In the illustrated and preferred embodiment (see FIG. 3), the low-G wall 36 of the first compartment 24 is offset toward the high-G wall 34, tapering into the compartment 24 in the direction of circumferential WB flow. In the illustrated and preferred embodiment (see FIG. 3), the low-G wall 36 also likewise tapers into the second compartment 26 in the direction of circumferential PRP flow.

In the illustrated and preferred embodiment (see FIG. 2), the dog leg portion of the RBC collection passage 56 and the dog leg portion of the PPP collection passage 64 are both tapered in width to present an enlarged cross section where they open into their respective chamber 24 and 26. The tapered widths of the passages 56 and 64 are each preferably gauged, relative to the inward radial taper of the low-G wall 36, to keep the cross sectional area of the RBC collection passage 56 and PPP collection passage 64 substantially constant.

The control of the cross section areas of the collection passages 56 and 64 keeps fluid resistance within the passages 56 and 64 relatively constant. It also maximizes the available separation and collection areas outside the passages 56 and 64. The tapered passages 56 and 64 also facilitate the removal of air from the assembly 18 during pre-processing priming.

The tapering low-G wall 36 in the first compartment 24 also preferably includes a stepped-up barrier 66 (see FIGS. 2 and 3) in the region where the RBC collection passage 56 opens into the compartment 24. The stepped-up barrier 66 extends from the low-G wall 36 across the entire chamber 24, as FIG. 2 shows. The stepped-up barrier 66 extends into the RBC mass formed during separation, creating a restricted passage 66 between it and the facing high-G wall 34 (see FIG. 3). The restricted passage 66 allows RBC present along the high-G wall 34 to move beyond the barrier 66 for collection by the RBC collection passage 56. Simultaneously, the stepped-up barrier 66 blocks the passage of the PRP beyond it, keeping the PRP within the dynamic flow conditions leading to the PRP collection region 50.

Flexible plastic tubing attached to the ports 38/40/42/44/46 interconnects the first and second chambers 24 and 26 with each other, with the second separation element 14, and with pumps and other stationary components located outside the rotating components of the centrifuge 30. The flexible tubing is ganged together into an umbilicus 70 (see FIGS. 4 to 6).

Figure 6:
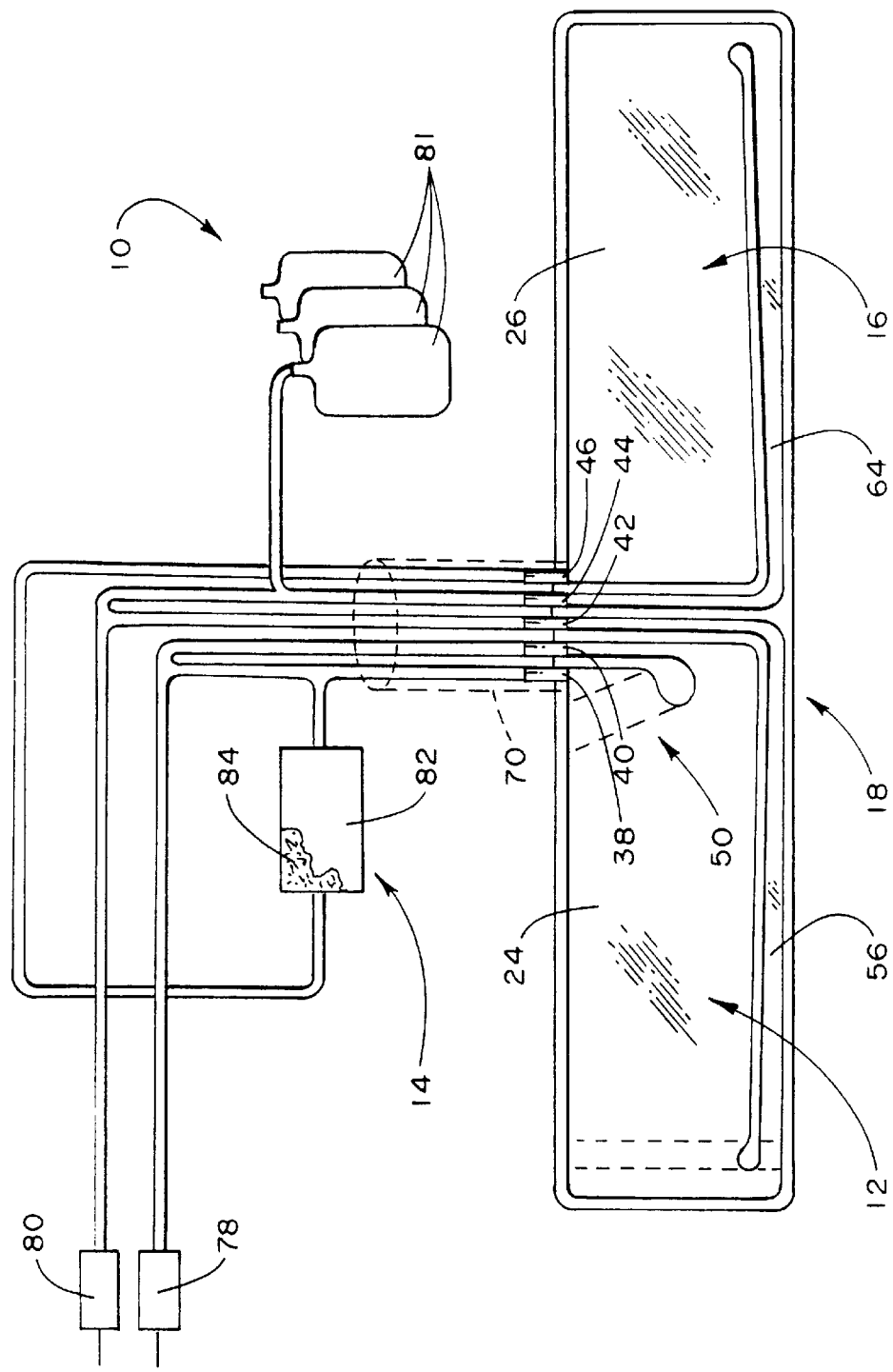
FIG. 6 is a partially diagrammatic view of a multi-stage two needle blood processing system that incorporates the separation elements shown in FIG. 4.

As FIG. 6 best shows, the non-rotating elements attached to the umbilicus 70 include the second separation element 14, the phlebotomy needles 78 and 80 that provide vein access to the donor, and the various containers 80 that provide or receive fluid during processing.

More particularly, the umbilicus 70 connects the WB inlet port 40 and the RBC collection port 42 of the rotating assembly 18 with stationary phlebotomy needles 78 and 80. One needle 78 continuously draws WB from the donor, while the other needle 80 continuously returns RBC to the donor. Alternatively, the system 10 could use a single phlebotomy needle to perform both functions in sequential draw and return cycles using conventional techniques.

The umbilicus 70 also connects the PRP collection port 38 of the first chamber 24 with the LDPRP inlet port 46 of the second chamber 26, via the second separation element 14, as FIG. 6 best shows. The second chamber 26 thereby receives LDPRP through the umbilicus 70 from the first chamber 24 (via the second separation element 14) for further separation into PPP and LDPC. As FIG. 6 also shows, a portion of the PRP exiting the PRP collection port 38 is diverted away from the second separation element 14 for recirculation directly back to the WB inlet port 40.

The umbilicus 70 also conveys separated PPP from the second chamber 26 through the associated PPP collection port 136. A portion of PPP is conveyed by the umbilicus 70 to the donor return needle 80. Another portion of PPP is conveyed by the umbilicus to one or more of the collection containers 81 for retention.

The LDPC remains behind in the second chamber 26 for later resuspension and collection, as will be described later.

As FIG. 5 shows, in operation, the centrifuge 30 suspends the rotor 28 in an upside down position during rotation, compared to the position shown in FIG. 4.

As FIG. 5 also shows, a non-rotating (zero omega) holder 72 holds the upper portion of the umbilicus 70 in a non-rotating position above the rotor 28.

Another holder 74 rotates the mid-portion of the umbilicus 70 at a first (one omega) speed about the rotor 28. Another holder 76 (see FIG. 4) rotates the lower end of the umbilicus 70 next to the assembly 18 at a second speed twice the one omega speed (the two omega speed), at which the rotor 28 also rotates. This known relative rotation of the umbilicus 74 and rotor 28 keeps the umbilicus 74 untwisted, in this way avoiding the need for rotating seals.

The dimensions of the various regions created in the processing chamber can, of course, vary according to the processing objectives. Table 1 shows the various dimensions of a representative embodiment of a processing assembly 18 of the type shown in FIGS. 2 and 3. Dimensions A through F referenced in Table 1 are identified in FIGS. 2 and 3.

TABLE 1

Overall length (A): 19½ inches
Overall height (B): 2¹³⁄₁₆ inches
First Stage Processing Chamber
   Length (C): 10⅛ inches
   Width (D): 2⅜ inches
   Maximum Radial Depth in Use: 4 mm Second Stage Processing Chamber
Length (E): 8¹³⁄₁₆ inches
Width (F): 2⅜ inches
Maximum Radial Depth in Use: 4 mm
Port Spacing (center line to center line): ⅜ inch In this configuration, the RBC collection passage 56 and the PPP collection passage 64 taper from a width of about ¼ inch to ⅛ inch. The restricted passage 68 in the first compartment 24 is about 1 mm to 2 mm in radial depth and about 1 mm to 2 mm in circumferential length.

In this configuration, when the rotor 28 is rotated at a speed of about 3400 RPM, a centrifugal force field of about 900 G's is generated along the high-G wall 34 of the chambers 24 and 26.

Alternatively, the system 10 can employ physically separate processing chambers as the first and third elements 12 and 16. Such elements could then be usable in association with a commercially available blood processing centrifuge, like the CS-3000® Blood Separation Centrifuge made and sold by the Fenwal Division of Baxter Healthcare Corporation (a wholly owned subsidiary of the assignee of the present invention). These alternative processing chambers are also disclosed in copending U.S. patent application Ser. No. 07/965,088, filed Oct. 22, 1992 and entitled "Enhanced Yield Platelet Collection Systems and Methods."

In the illustrated and preferred embodiment, the system 10 carries out blood component separation in the second element 14 using filtration.

Still, the second element 14 can use other separation techniques. The second element 14 can separate leukocytes by centrifugation, absorption, columns, chemical, electrical, and electromagnetic means.

In the illustrated and preferred embodiment, the second element 14 comprises a filter device 82 that employs a non-woven, fibrous filter media 84.

The composition of the filter media 84 can vary. In the illustrated and preferred embodiment, the media 84 comprises fibers that contain nonionic hydrophillic groups and nitrogen-containing basic functional groups. Fibers of this type are disclosed in Nishimura et al U.S. Pat. No. 4,936,998, which is incorporated herein by reference. Filter media 84 containing these fibers are commercially sold by Asahi Medical Company in filters under the tradename SEPACELL.

Filter media 84 containing these fibers have demonstrated the capacity to remove leukocytes while holding down the loss of platelets.

Figure 7:
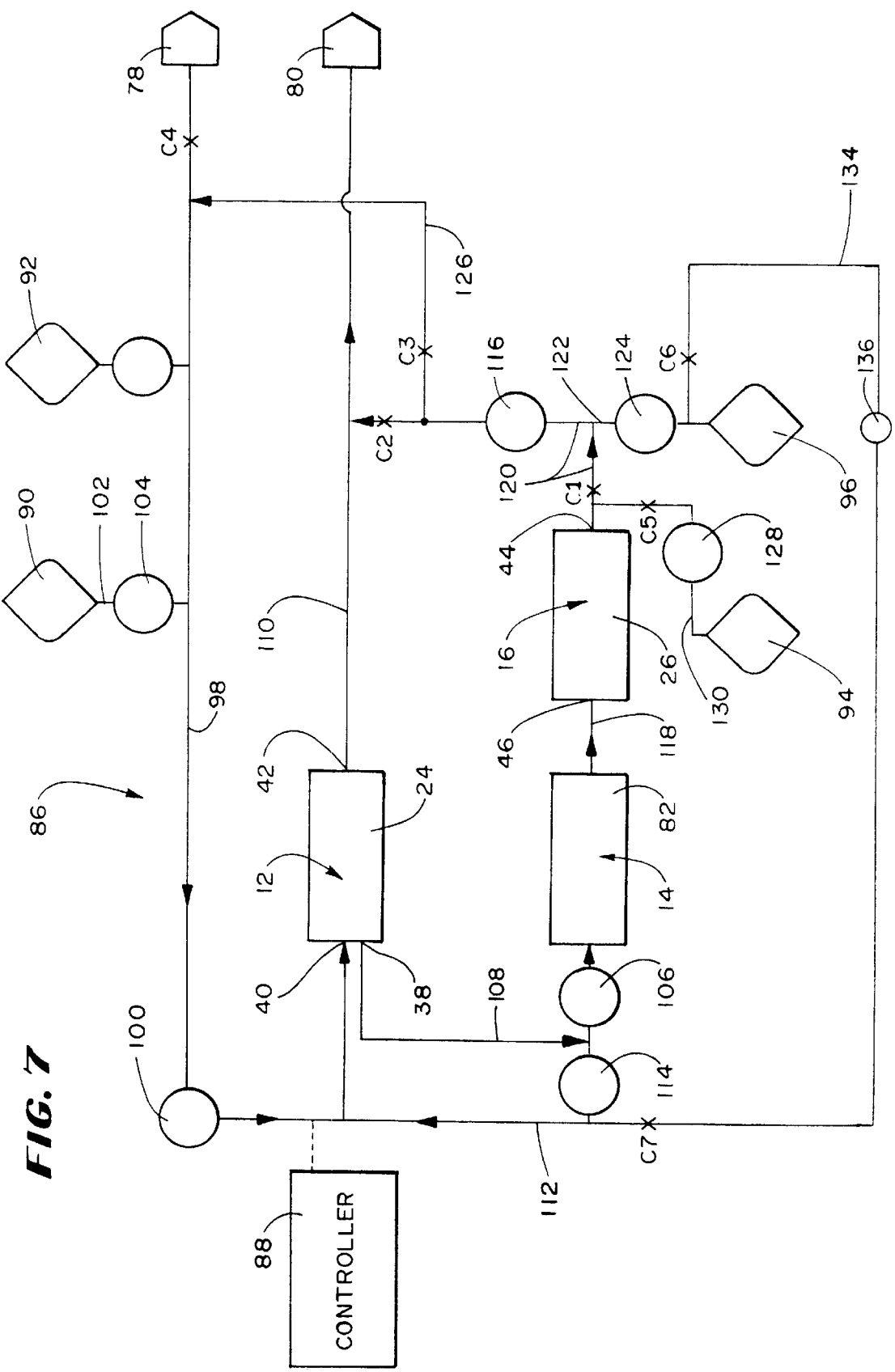
FIG. 7 is a diagrammatic view of the two needle blood processing system shown in FIG. 6.

The system 10 shown in FIGS. 1 to 6 can be readily incorporated into a continuous single or double needle on line blood processing systems. FIG. 7 shows in diagrammatic form a representative continuous two needle on line processing system 86 that carries out an automated resuspended platelet collection procedure employing the features of the invention.

A processing controller 88 operates the two needle system 86 in continuous collection and return cycles, which occur simultaneously. As used in this Specification, the terms "continuous" and "simultanenous" are not meant to be limited to sequences that are continuous or simultaneous only in the quantitative sense. The terms are meant to encopmass sequences that, while not absolutely continuous or simultaneous quantitatively, are "substantially" continuous or simultaneous in a qualitative sense, when there is no significant operational or therapuetic difference in terms of the way they operate and the function and result achieved.

In the collection cycle, the donor's WB is continuously supplied through the draw needle 78 to the processing compartment 24 (for separation into RBC and PRP), while continuously conveying PRP from the compartment 24 into the filter device 82 (for creating LDPRP), and while continuously conveying LDPRP from the filter device 82 into the compartment 26 (for separation into LDPC and PPP).

During the return cycle, which in the two needle system 86 occurs simultaneously with the collection cycle, the controller 88 continuously returns RBC from the compartment 24 and a portion of the PPP from the compartment 26 to the donor through the return needle 80.

Throughout the processing period, the circulatory system of the donor remains connected in communication with the system 86 through the needles 78 and 80.

The controller 88 also continuously retains a portion of the PPP exiting the compartment 26, diverting it from return to the donor, during the entire period that LDPC is being separated in the compartment 26. The system 86 retains the diverted PPP for long term storage, as well as to aid processing and resuspension of LDPC in the compartment 26 for long term storage as RES-LDPC.

The system 86 includes a container 90 that holds anticoagulant. While the type of anticoagulant can vary, the illustrated embodiment uses ACDA, which is a commonly used anticoagulant for pheresis.

The system 86 also includes a container 92 that holds saline solution for use in priming and purging air from the system 86 before processing begins.

The system 86 also includes one or more collection containers 94 for receiving RES-LDPC for therapeutic use, with or without long term storage. The system 86 also includes one (or optionally more) collection container 96 for retaining PPP during processing. The container 96 ultimately can also serve as a long term storage container for retained PPP.

Under the control of the controller 88, a first tubing branch 98 and a WB inlet pumping station 100 direct WB from the draw needle 78 to the WB inlet port 40 of the first stage processing chamber 24. The WB inlet pumping station 100 operates continuously at, for example, 50 ml/min. Meanwhile, an auxiliary tubing branch 102 meters anticoagulant to the WB flow through an anticoagulant pumping station 104.

ACDA anticoagulant can be added to constitute about 9% of the entry WB. Saline dilution fluid can also be added in an amount representing about 4% of donor body volume (i.e., 200 ml saline for 5000 ml in body volume).

Anticoagulated WB enters and fills the first processing chamber 24 in the manner previously described. There, centrifugal forces generated during rotation of the chamber assembly 18 separate WB into RBC and PRP.

The controller 88 operates a PRP pumping station 106 to draw PRP from the PRP collection port 38 into a second tubing branch 108.

The processing controller 88 monitors the location of the interface on the ramp 58. It varies the speed of the PRP pumping station 106 to keep the interface at a prescribed location on the ramp 58. The controller 88 also limits the maximum rate of the variable PRP pumping station 106 (for example, 25 ml/min) to be less than the WB inlet pumping station 100.

Meanwhile, a third tubing branch 110 conveys the RBC from the RBC collection port 42 of the first stage processing chamber 24. The third tubing branch 110 leads to the return needle 80 to return RBC to the donor.

The system 86 includes a recirculation tubing branch 112 and an associated recirculation pumping station 114. The processing controller 88 operates the pumping station 114 to divert a portion of the PRP exiting the PRP collection port 38 of the first processing compartment 24 for remixing with the WB entering the WB inlet port 94 of the first processing compartment 24.

The controller 88 can control the recirculation of PRP in different ways.

In the illustrated and preferred embodiment, the pumping rate of the recirculation pump 114 is maintained as a percentage ($\%_{RE}$) of the pumping rate WB inlet pump 100 governed as follows:

$$\%_{RE} = K * Hct-100$$

where:

Hct is the hematocrit of the donor's whole blood, measured before donation, and

K is a dilution factor that takes into account the volume of anticoagulant and other dilution fluids (like saline) that are added to the donor's whole blood before separation.

When the pumping rate of the recirculation pump 114 is maintained at the predetermined percentage ($\%_{RE}$) of the pumping rate WB inlet pump 100, a surface hematocrit of about 30% to 35% is maintained in the WB entry region of the first compartment 24. The preferred surface hematocrit in the entry region is believed to be about 32%.

Keeping the surface hematocrit in the entry region in the desired range provides maximal separation of RBC and PRP.

The value of the dilution factor K can vary according to operating conditions. The inventor has determined that K=2.8, when ACDA anticoagulant is added to constitute about 9% of the entry whole blood volume, and a saline dilution fluid is added in an amount representing about 4% of donor body volume (i.e., 200 ml saline for 5000 ml in body volume).

By mixing PRP with the WB entering the first processing compartment 24 to control surface hematocrit in the entry region, the velocity at which RBC settle toward the high-G wall 66 in response to centrifugal force increases. This, in turn, increases the radial velocity at which plasma is displaced through the interface toward the low-G wall 64. The increased plasma velocities through the interface elute platelets from the interface. As a result, fewer platelets settle on the interface.

The remainder of the PRP exiting the first compartment 24 enters the filter device 82 (by operation of the pumping station 106) for removal of leukocytes. A preferred flow rate of PRP through the filter device 82 is in the range of 15 to 30 ml/minute.

The continuous on-line removal of leukocytes from PRP that the invention provides does not activate platelets carried in the PRP.

The concurrent recirculation of a portion of the PRP away from the filter device 82 reduces the overall flow volume load on the filter device 82. This, in turn, enhances the leukocyte removal efficiencies of the filter device 82.

A fourth tubing branch 118 conveys LDPRP to the LDPRP inlet port 46 of the second stage processing chamber 26. There, LDPRP undergoes further separation into LDPC and PPP, as earlier described.

PPP exits the PPP collection port 44 of the second stage processing chamber 26 through a fifth tubing branch 120. The fifth tubing branch 120 joins the third tubing branch 110 (carrying RBC), which leads to the return needle 80.

The system 86 includes a sixth tubing branch 122 and an associated pumping station 124 for continuously retaining a portion of the PPP during the entire processing period.

The processing controller 88 operates the PPP retaining pumping station 124 throughout the period that separation occurs within the compartment 26 to continuously divert a prescribed portion of the PPP exiting the PPP collection port 44 away from the third tubing branch 110. The sixth tubing branch 122 continuously conveys the diverted PPP to the collection container 96 for retention.

As before stated, the remainder of the PPP exiting the second compartment 26 enters the third branch 110, where it joins the RBC for return to the donor by operation of the PPP return pump station 116.

The processing controller 88 controls the flow rate of the pumping station 124 to retain the desired proportional volume of PPP separated in the second chamber 26. The system 86 returns the remaining PPP to the donor.

In the preferred embodiment, the controller 88 incorporates a PPP retention control process 132 (see FIG. 8) that governs the rate at which PPP should be retained (expressed in ml/min) during the processing period to collect the volume of PPP desired by the end of the processing period. The control process not only takes into account the physical operating parameters of the system 86, but it also takes into account the physiology and comfort of the individual donor.

Figure 8:
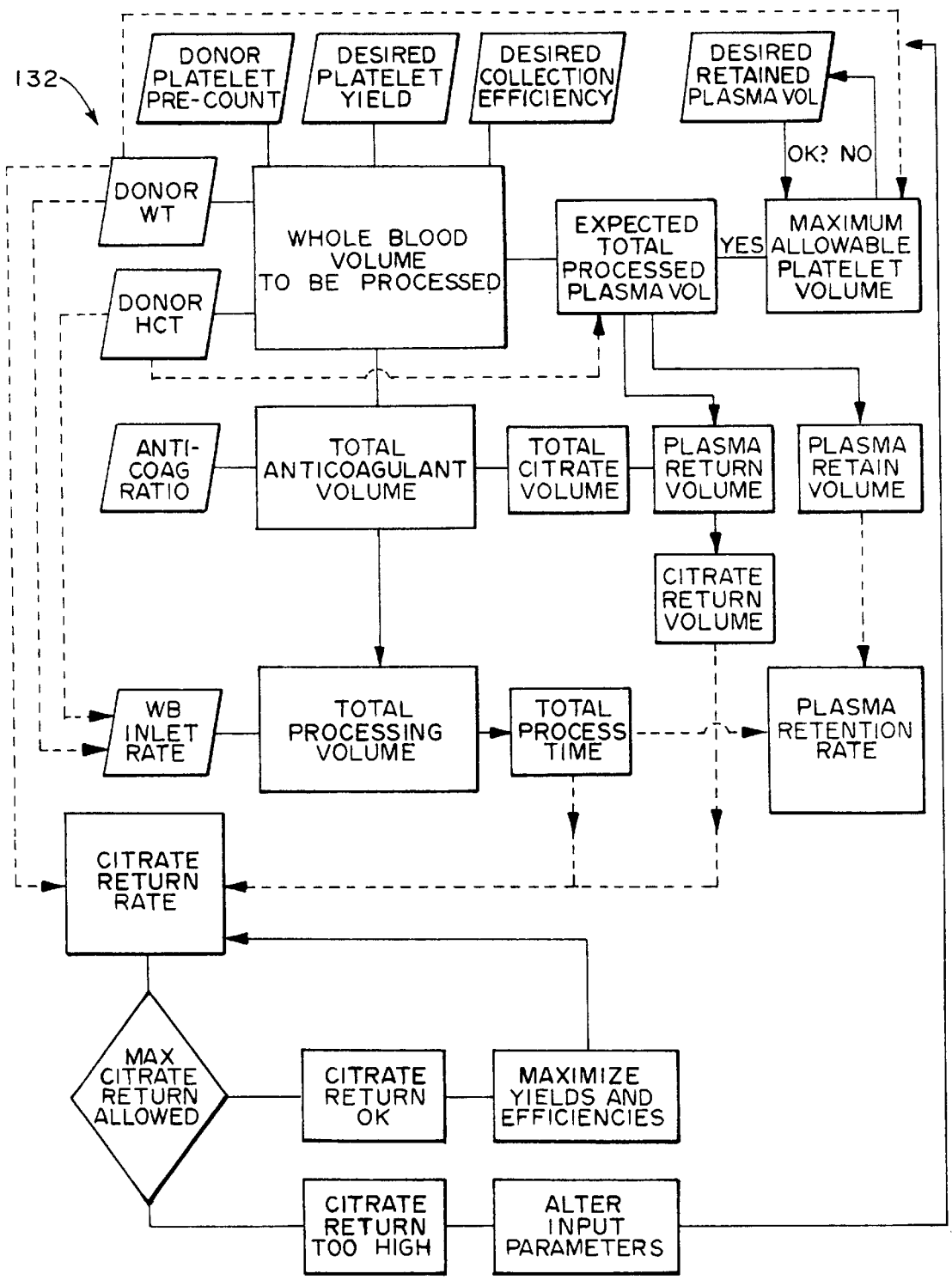
FIG. 8 is a diagrammatic view of a process for controlling the return and retention of platelet-poor plasma in the system shown in FIG. 7.

As FIG. 8 shows, the control process 132 receives as input the donor's weight; the donor's platelet count (before donation); the desired platelet yield; and the targeted system efficiency. The system efficiency is expressed as the percentage of the platelets processed that are ultimately collected as LDPC.

Taking these parameters into consideration, the control process 132 determines the total WB volume that should be processed to obtain the desired platelet yield.

From the total WB volume, the control process 132 derives the total PPP volume. The plasma volume is derived by multiplying the total WB volume by (1.0−Hct), where Hct is expressed in decimal form (e.g., 0.4 instead of 40%).

The control process 132 also receives as input the amount of PPP the operator wants to retain during processing. The control process 132 first compares the desired PPP retention volume to the maximum volume of PPP that, under applicable governmental regulations, can be retained. In the United States, for example, the Food and Drug Administration limits the volume of plasma that can be collected from a donor during a given procedure to 600 ml for donors with a body weight less than 175 pounds, and 750 ml from a donor with a body weight equal to or greater than 175 pounds.

If the desired PPP retention volume does not exceed the maximum allowable retention volume, the control process 132 subtracts the desired PPP volume from the total PPP volume to derive the PPP return volume. Otherwise, the control process 132 generates an error signal, informing the user that less PPP must be retained.

The control process 132 uses the donor's hematocrit (Hct) and the selected anticoagulant ratio to set a WB flow rate the donor should be able to tolerate. A look up table can be empirically prepared to correlate WB flow rates with these factors.

Alternatively, the user can select a nominal WB flow rate based upon experience (say, 50 to 60 ml/min). The user can then make on line adjustments as necessary during processing based upon the observed response of the donor.

Based upon the WB processing volume and the selected anticoagulant ratio, the control process 132 determines the volume of anticoagulant that will be mixed with WB during processing.

The control process 132 adds together the total WB processing volume and the total anticoagulant volume (plus any dilution fluids, if added) to determine the total fluid volume that will be processed. By dividing the total fluid volume by the WB flow rate, the control process 132 calculates the total processing time.

Based upon dividing the desired PPP retention volume by the derived processing time, the control process 132 derives the rate at which the PPP retention pump 124 must be operated.

The control process 132 also determines the effect of the PPP retention rate upon the rate at which the donor receives citrate in the portion of PPP that is returned to the donor. The control process adjusts the derived PPP retention rate as necessary to avoid a citrate return rate that is higher than a preset, physiologically relevant value.

Based upon the total volume of anticoagulant and the type of the anticoagulant, the control process 132 determines the total volume of citrate that will be mixed with WB.

The proportion of citrate contained in anticoagulants is known. For example, ACDA anticoagulant contains 21.4 mg of citrate for each ml of solution.

Based upon the proportion of PPP that will be returned to the donor, the control process 132 derives the rate at which the system will infuse the citrate into the donor. The control process 132 derives the citrate infusion rate in terms of the amount of citrate (in mg) the donor receives with the returned PPP per unit of donor body weight (in kg) per unit of processing time (in minutes).

The control process 132 compares the derived citrate infusion rate to a nominal citrate infusion rate, which is also expressed in mg citrate per kg body weight per minute of processing time. The nominal citrate infusion rate represents a predetermined maximum rate that citrate can be infused in a typical donor without causing donor discomfort and other citrate-related reactions. The control process 132 in the illustrated and preferred embodiment sets the nominal citrate infusion rate at 1.2 mg/kg/min, which is based upon empirical data.

As long as the targeted PPP retention rate results in a citrate infusion rate that is equal to or less than 1.2 mg/kg/min, the controller 88 is free to adjust the operating parameters of the system 86 as necessary to maximize the component yields and processing efficiencies.

However, if a targeted PPP retention rate results in a citrate infusion rate that exceeds 1.2 mh/kg/min, the controller 88 adjusts the processing parameters to lower the citrate infusion rate.

The control process 132 shown in FIG. 8 can be expressed in various ways in terms of a series of simultaneous equations that, when solved, derive the operating parameters listed above. The equations can be solved recursively during processing to take into account changes in Hct and platelet counts in the donor's WB.

The continuous retention of PPP serves multiple purposes, both during and after the component separation process.

The retention of PPP serves a therapeutic purpose during processing. PPP contains most of the anticoagulant that is metered into WB during the component separation process. By retaining a portion of PPP instead of returning it all to the donor, the overall volume of anticoagulant received by the donor during processing is reduced. This reduction is particularly significant when large blood volumes are processed.

By continuously diverting PPP away from the donor throughout the separation process, the donor realizes this benefit continuously throughout the processing period, provided that the nominal citrate infusion rate is not exceeded. The monitoring function that control process 132 performs assures that this benefit will be obtained.

Also the retention of PPP during processing keeps the donor's platelet count higher and more uniform during processing. This is because the donor receives back less fluid volume during the processing period, thereby reducing the dilution of whole blood undergoing processing.

EXAMPLE 2

This Example demonstrates the results obtained by operation of the control process 132 shown in FIG. 8 in connection with a platelet collection procedure for a representative donor.

In this Example, the donor is assumed to have a body weight of 125 lbs (56.3 kg). The donor is also assumed to have a preprocessing Hct of 40% and a preprocessing platelet count of 250,000 per $\mu$l.

In this Example, the desired platelet yield for the process is $4.0 \times 10^{11}$; and the desired system efficiency is 90%. ACDA anticoagulant is used at a WB-to-anticoagulant ratio of 9%.

Based upon the above assumptions, the control process derives 2.0 L as the total WB volume that must be processed. The total volume of PPP associated with this WB volume is 1200 ml.

Based upon the 9% anticoagulant ratio, the control process 132 derives 180 ml as the volume of anticoagulant that will be added. The total processing volume is therefore 2180 ml. The total citrate volume is 3.852 g.

The user sets 60 ml/min as the nominal WB inlet flow rate. At this rate, the processing time will be 36.3 minutes.

The user seeks to ultimately retaining 500 ml of PPP during processing, which is well short of the prescribed maximum for the donor's body weight. With a processing time of 36.3 minutes, the PPP retention pump must be operated at a rate of 13.8 ml/min throughout the process to collect the desired PPP volume of 500 ml.

The remaining 700 ml will be returned to the donor. This means that the donor will receive only about 58% (7/12th) of the total anticoagulant volume that would have been received, if the system 86 retained no PPP.

Moreover, when 500 ml of PPP is retained, the total fluid volume returned to the donor is just ¾ of the total drawn volume. In a single needle system, each return cycle would take less time and allow an overall higher blood flow rate.

The control process 132 derives the citrate infusion rate by first determining the volume of citrate that the returned PPP will carry, which is 2.247 g (7/12th of 3.852 g). The control process 132 then divides the returned citrate volume by the donor's body weight (56.3 kg) and by the processing time (36.3 min) to obtain a citrate return rate of 1.1 mg/kg/min.

The control process 132 determines that the citrate return rate is less than the nominal 1.2 mg/kg/min. The PPP retention pump 124 can thereby be operated at 13.8 ml/min without anticipating adverse donor citrate-related reactions.

The system 86 also derives processing benefits from the retained PPP.

ALTERNATIVE RECIRCULATION MODE

The system 86 can, in an alternative recirculation mode, recirculate a portion of the retained PPP, instead of PRP, for mixing with WB entering the first compartment 24.

In this mode, the system 86 opens clamps C6 and C7 to convey retained PPP from the container 96 through a PPP recirculation branch 134 (see FIG. 7) and associated pumping station 136 into the recirculation branch 112.

The controller 88 controls the pumping station 136 in the same manner described for pumping station 114 to mix retained PPP with the incoming WB entering the first compartment 24.

KEEP-OPEN MODE

Should WB flow be temporarily halted during processing, the system 86 enters a "keep-open" mode. In this mode, the system 86 draws upon the retained volume of PPP as an anticoagulated "keep-open" fluid.

More particularly, the system controller 88 closes clamps C1 and C2, opens clamp C3, and operates the pump 116 to direct a volume of the PPP from the container 96 through a keep open tubing branch 126, which communicates with the WB tubing branch 98. The anticoagulant present in the PPP keeps the WB tubing branch 98 open and patent until the flow of anticoagulated WB resumes.

The system controller 88 keeps the return needle 80 open and patent by intermittently closing clamp C3 and opening clamp C2 to provide a keep open flow of anticoagulated PPP through the return needle 80.

Use of PPP as a keep-open fluid avoids the need to introduce additional anticoagulant from container 90 for this purpose.

RINSE-BACK MODE

The system 86 also enters a "rinse-back" mode at the end of the separation process. In this mode, the system 86 draws upon the retained volume of PPP as a "rinse-back" fluid.

More particularly, the system controller 88 stops the flow of WB through the tubing branch 98 by closing clamp C4. The system controller 88 closes the clamp C2, opens clamp C3, and operates the pump 116 to direct a volume of the collected PPP into the first separation compartment 24 through tubing branches 122, 120, 126 and 98. The flow of PPP resuspends and purges RBC from the compartment 24 for return to the donor through the return branch 110.

Because PPP, and not saline, is the rinse-back fluid, downstream component separation through the filter device 82 and the second compartment 26 can continue without interruption during the rinse-back mode. The PPP volume used for rinse-back purposes ultimately returns, after separation in the first compartment 24 and flow through the second compartment 26, to the source PPP retention container 96.

RESUSPENSION MODE

The system 86 also operates in a resuspension mode to draw upon a portion of the retained PPP to resuspend LDPC in the second compartment 24 for transfer and storage as RES-LDPC in the collection container(s) 94.

In this mode, the system controller 88 closes clamps C2, C3, and C5, while opening clamp C1. The controller 88 operates the pump 124 to convey a volume of retained PPP through the PPP collection port 44 into the second compartment 26. This returned PPP volume mixes with and resuspends LDPC in the second compartment 26.

Preferably, during the resuspension period, the compartment 26 is not rotated at high speeds. Instead, as PPP is conveyed into the second compartment 26, the rotor 28 slowly oscillates the assembly 18 first in one rotational direction and then in an opposite rotational direction. The oscillation creates constantly changing acceleration or agitation forces that aid the mixing and resuspension process within the second compartment 26.

Also, a substantial portion of the fluid volume residing with the LDPC in the second compartment 26 is preferably drawn away before introducing the resuspension volume of PPP. The controller 88 operates the pump 124 to convey this residual fluid volume from the second compartment 26 into the PPP retention container 96.

In the illustrated and preferred embodiment, the second chamber 26 contains about 40 ml of PPP at the end of the processing period. About 20 ml of the residual fluid volume is conveyed away before resuspending the LDPC.

The second compartment 26 is therefore about half empty of residual fluid when the resuspension process begins. This fluid-depleted condition concentrates the volume of LDPC to intensify the acceleration forces generated when the compartment 26 is oscillated. This further enhance the mixing and resuspension process.

In the illustrated and preferred embodiment, about 20 ml of PPP is returned and used as a resuspension fluid. After a predetermined mixing period, the system controller 88 closes clamp C1, opens clamp C5, and operates the RES-LDPC pumping station 128. This conveys the RES-LDPC volume out the PPP collection port 44 through a RES-LDPC collection tubing branch 130 into the container(s) 94 for storage.

In a preferred implementation, the resuspension mode constitutes a series of sequential resuspension batches. In each batch, the residual fluid volume of the second compartment 26 is depleted by about 20 ml, and the assembly 18 is oscillated, and a prescribed aliquot of about 20 ml PPP is conveyed into it.

Following a set mixing period, a volume of LDPC that is resuspended is conveyed out of the second compartment 26 and into the container(s) 94. These sequential batches repeat, until all the volume of LDPC is suspended and conveyed as RES-LDPC into the collection container(s) 94.

At the end of the resuspension process, a resuspension volume of PPP (typically about 200 ml) resides with the RES-LDPC to serve as a storage medium. Typically, about $4.0 \times 10^{11}$ platelets are suspended in this fluid volume.

The remaining volume of retained PPP is stored in the container 96 for subsequent therapeutic use.

The system 86 thereby boosts the yield of usable therapeutic components during a given collection procedure.

In a single needle collection system (not shown) that embodies the features of the invention, a return cycle does not occur simultaneously with a collection cycle. Instead, the single system repeatedly toggles between a collection cycle and a return cycle.

During a given collection cycle, WB is drawn through the single needle, and the separated RBC and a portion of the separated PPP are temporarily pooled in reservoirs. When a preselected volume of RBC is pooled in this manner, the associated controller switches to a return cycle. In the return cycle, the WB flow from the donor is suspended, while the pooled RBC and PPP are returned to the donor through the same single needle.

In a single needle system, processing can continue uninterrupted through the compartment 24, filter device 82, and the compartment 26 during a return cycle by collecting a quantity of WB in a reservoir upstream of the compartment 24 during the collection cycle. The single needle system then draws WB from the reservoir for processing during a return cycle.

A single needle system also retains a portion of the PPP exiting the compartment 26, diverting it from pooling and return to the donor, during the entire period that LDPC is being separated in the compartment 26. The retained PPP is used for the same purposes in a single needle system as in a two needle system.

The chamber assembly 18, the associated containers, and the interconnecting tubing branches associated with the system can be made from conventional approved flexible medical grade plastic materials, such as polyvinyl chloride plasticized with di-2-ethyl-hexylphthalate (DEHP).

Preferable, the container(s) 94 intended to store the resuspended LDPC, are made of polyolefin material (as disclosed in Gajewski et al U.S. Pat. No. 4,140,162) or a polyvinyl chloride material plasticized with tri-2-ethylhexyl trimellitate (TEHTM). These materials, when compared to DEHP-plasticized polyvinyl chloride materials, have greater gas permeability that is beneficial for platelet storage.

Various features of the inventions are set forth in the following claims.

I claim:

1. A system for obtaining a platelet-rich concentrate having a reduced number of leukocytes comprising
    a first separation chamber having an entry region to receive whole blood containing leukocytes to separate the whole blood into a first layer comprising red blood cells, a second layer comprising a suspension of platelets, and an interface between the first and second layers, the first separation chamber including a collection region to collect the suspension of platelets and an outlet communicating with the collection region,
    a second separation chamber to separate the suspension of platelets into a platelet-rich concentrate and platelet-poor component,
    a filter for removing leukocytes from the suspension of platelets, the filter having an inlet and an outlet,
    a first path communicating with the first separation chamber and a source of whole blood including a first pump to convey whole blood through the first path into the entry region of the first separation chamber,
    a second path communicating with the outlet of the first separation chamber and the filter inlet including a second pump to convey platelet suspension from the collection region into the filter,
    a third path communicating with the second separation chamber and the filter outlet to convey filtered platelet suspension from the filter into the second separation chamber,
    a monitoring element monitoring location of the interface within the collection region and transmitting location signals, and
    a controller coupled to the monitoring element and to the second pump and operating the second pump at a pumping rate that varies to maintain the location of the interface at a desired location in the collection region spaced from the outlet.

2. A system according to claim 1
    wherein the first path remains in communication with the whole blood source substantially throughout the separation process.

3. A system according to claim 1
    wherein the first and second separation chambers rotate in a rotational field about an axis, and
    wherein the filter is located outside the rotational field.

4. A method for obtaining a platelet-rich concentrate having a reduced number of leukocytes comprising
    (a) introducing whole blood containing leukocytes from a source at a selected first pumping rate into a first separation chamber,
    (b) separating the whole blood in the first separation chamber into a first layer comprising a suspension of platelets, a second layer comprising red blood cells, and an interface between the first and second layers,
    (c) conveying the suspension of platelets at an outlet pumping rate from the first separation chamber into a second separation chamber while simultaneously filtering the suspension of platelets to reduce the number of leukocytes,
    (d) monitoring the location of the interface within the first separation chamber and varying the outlet pumping rate to maintain the interface within the first separation chamber while conveying the suspension of platelets from the first separation chamber, and
    (e) separating the filtered suspension of platelets in the second separation chamber into a platelet-rich concentrate and platelet-poor component.

5. A method according to claim 4
    wherein step (a) includes the step of (f) establishing communication between the whole blood source and the first separation chamber,
    and further including the step of (g) maintaining the communication established between the whole blood source and the first separation chamber substantially throughout steps (b) and (e).

6. A method according to claim 4
    wherein, during steps (b) and (e), the first and second separation chambers rotate about an axis in a centrifugal field, and
    wherein, while filtering the platelet suspension during step (c), the platelet suspension is located outside the centrifugal field.

* * * * *

UNITED STATES PATENT AND TRADEMARK OFFICE
CERTIFICATE OF CORRECTION

PATENT NO.    : 5,804,079
DATED         : September 8, 1998
INVENTOR(S)   : Richard I. Brown It is certified that error appears in the above-identified patent and that said Letters Patent is hereby corrected as shown below:

Column 4,
Line 64, delete "ml" and substitute -- $\mu$l --

Column 9,
Line 61, delete "encopmass" and substitute -- encompass --

Column 14,
Line 31, delete "retaining" and substitute -- retains --

Column 16,
Line 16, delete "enhance" and substitute -- enhances --

Signed and Sealed this

Twenty-ninth Day of June, 2004

JON W. DUDAS
*Acting Director of the United States Patent and Trademark Office*